United States Patent
Heidtkamp et al.

(10) Patent No.: US 12,345,215 B2
(45) Date of Patent: Jul. 1, 2025

(54) EXHAUST-GAS SENSOR FOR AN INTERNAL COMBUSTION ENGINE

(71) Applicant: Vitesco Technologies GmbH, Regensburg (DE)

(72) Inventors: Christian Heidtkamp, Munich (DE); David Wieland, Munich (DE); Johannes Bentner, Munich (DE)

(73) Assignee: VITESCO TECHNOLOGIES GMBH, Regensburg (DE)

( * ) Notice: Subject to any disclaimer, the term of this patent is extended or adjusted under 35 U.S.C. 154(b) by 0 days.

(21) Appl. No.: 18/709,943

(22) PCT Filed: Nov. 7, 2022

(86) PCT No.: PCT/EP2022/081005
§ 371 (c)(1),
(2) Date: May 14, 2024

(87) PCT Pub. No.: WO2023/083757
PCT Pub. Date: May 19, 2023

(65) Prior Publication Data
US 2025/0012227 A1  Jan. 9, 2025

(30) Foreign Application Priority Data
Nov. 15, 2021  (DE) .............. 10 2021 212 821.1

(51) Int. Cl.
*F02D 41/14* (2006.01)
*G01N 27/419* (2006.01)
(Continued)

(52) U.S. Cl.
CPC ....... *F02D 41/146* (2013.01); *F02D 41/1493* (2013.01); *G01N 27/419* (2013.01); *G01N 33/0037* (2013.01); *F02D 2041/281* (2013.01)

(58) Field of Classification Search
CPC .............. F02D 41/146; F02D 41/1493; F02D 2041/281; G01N 27/419; G01N 33/0037
See application file for complete search history.

(56) References Cited

U.S. PATENT DOCUMENTS 6,036,841 A * 3/2000 Kato ................... G01N 27/419
204/426
10,082,480 B2  9/2018 Abe
(Continued)

FOREIGN PATENT DOCUMENTS

| CN | 107748191 A | 3/2018 |
| CN | 109375513 B | 2/2019 |

(Continued)

OTHER PUBLICATIONS

Search Report for International Application No. PCT/EP2022/081005, 11 pages, Mar. 23, 2023.
(Continued)

*Primary Examiner* — Audrey B. Walter
(74) *Attorney, Agent, or Firm* — Slayden Grubert Beard PLLC

(57) ABSTRACT

Some embodiments of the teachings herein include methods for operating an exhaust gas sensor with a pump electrode, a measuring electrode, and a reference electrode. An example includes: discharging oxygen from the measuring cavity by applying a measurement current to the measuring electrode so a measurement voltage between the measuring electrode and the reference electrode is kept at a predetermined first setpoint value; discharging oxygen from the pump cavity by applying a pump current to the pump electrode so an electrode voltage between the pump electrode and the reference electrode is kept at a predetermined second setpoint value; determining a nitrogen oxide value based at least in part on a value of the measurement current; adapting the first setpoint value for the measurement voltage (Continued)

based on the determined nitrogen oxide value; and/or adapting the second setpoint value for the electrode voltage based on the determined nitrogen oxide value.

8 Claims, 2 Drawing Sheets

(51) Int. Cl.
*G01N 33/00* (2006.01)
*F02D 41/28* (2006.01)

(56) References Cited

U.S. PATENT DOCUMENTS

| | | | |
|---|---|---|---|
| 10,634,643 | B2 | 4/2020 | Kayama |
| 11,531,014 | B2 | 12/2022 | Watanabe |
| 11,959,877 | B2 | 4/2024 | Watanabe |
| 2003/0121310 | A1* | 7/2003 | Tomura ................ G01N 27/419 73/31.05 |
| 2009/0242426 | A1 | 10/2009 | Kilinc |
| 2017/0336344 | A1 | 11/2017 | Uemura |
| 2020/0319139 | A1* | 10/2020 | Zhang ................... F01N 11/007 |
| 2021/0109058 | A1* | 4/2021 | Watanabe .......... G01N 33/0006 |
| 2021/0278386 | A1* | 9/2021 | Zhang ................. G01N 27/419 |
| 2023/0128576 | A1 | 4/2023 | Wieland |

FOREIGN PATENT DOCUMENTS

| | | | |
|---|---|---|---|
| CN | 110735699 B | 1/2020 | |
| DE | 102005029556 B3 | 9/2006 | |
| DE | 102008006633 A1 | 7/2009 | |
| DE | 102016206991 A1 | 10/2017 | |
| DE | 102017110515 A1 | 11/2017 | |
| DE | 102017110519 A1 | 11/2017 | |
| DE | 102017209300 A1 | 12/2018 | |
| DE | 102018203313 A | 9/2019 | |
| DE | 102018203394 A | 9/2019 | |
| DE | 102019203749 A1 | 4/2020 | |
| DE | 102019209456 B3 * | 6/2020 | ........... G01N 27/419 |
| DE | 102019203707 B3 | 7/2020 | |
| DE | 102019203704 A1 | 9/2020 | |
| DE | 102020005125 A1 | 3/2021 | |
| DE | 112019003230 T5 | 3/2021 | |
| DE | 102020204213 A1 | 10/2021 | |
| EP | 0845670 A2 | 3/1998 | |
| EP | 3163297 A1 | 3/2017 | |
| EP | 3477068 A1 | 1/2019 | |
| WO | 2019109782 A1 | 6/2019 | |
| WO | 2020260330 A1 | 12/2020 | |

OTHER PUBLICATIONS

Office Action for DE Patent Application No. 10 2021 212 821.1, 10 pages, May 12, 2022.

* cited by examiner

EXHAUST-GAS SENSOR FOR AN INTERNAL COMBUSTION ENGINE

CROSS-REFERENCE TO RELATED APPLICATIONS

This application is a U.S. National Stage Application of International Application No. PCT/EP2022/081005 filed Nov. 7, 2022, which designates the United States of America, and claims priority to DE Application No. 10 2021 212 821.1 filed Nov. 15, 2021, the contents of which are hereby incorporated by reference in their entirety.

TECHNICAL FIELD

The present disclosure relates to sensors. Various embodiments of the teachings herein include systems and/or methods for operating an exhaust gas sensor, for example a nitrogen oxide sensor, for an internal combustion engine.

BACKGROUND

Exhaust gas sensors, such as nitrogen oxide sensors, lambda probes, and oxygen sensors, for example, may be based on the amperometric principal, an method electrochemical for quantitatively determining chemical substances. In particular, an electric current is set at an electrode of the exhaust gas sensor in such a way that an electrochemical potential that is constant over time is established. By way of example, nitrogen oxide sensors allow a measurement of the nitrogen oxide concentration in the exhaust gas of internal combustion engines, for example gasoline or diesel engines. This enables, for example, optimum control and diagnosis of nitrogen oxide catalytic converters by the engine controller.

Exhaust gas sensors of this type comprise a main body formed from a solid electrolyte, in which cavities with assigned electrodes are provided. In addition, a heating device is arranged in the main body and is designed to heat the main body to a predetermined operating temperature and to keep it there, for example at about 850° C. Furthermore, in the case of exhaust gas sensors, in particular nitrogen oxide sensors, it is known practice to operate these in such a way that predetermined setpoint values for open-loop control or closed-loop control of what are known as Nernst voltages are unchangeable over the service life of the exhaust gas sensor, in particular nitrogen oxide sensor, and therefore an optimum between the balance of oxygen and nitrogen oxide is set. The oxygen concentrations and therefore the decomposition of the oxygen and nitrogen oxide molecules in the individual cavities of the exhaust gas sensor, in particular nitrogen oxide sensor, are determined by way of the Nernst voltages.

Further exhaust gas sensors and methods for operating exhaust gas sensors are disclosed in DE 10 2018 203 394 A1, CN 109 375 513 B, CN 110 735 699 B, DE 10 2018 203 313 A1, DE 10 2017 209 300 A1 and WO 2020/260330 A1.

SUMMARY

The teachings of the present disclosure include specifying a method for operating an exhaust gas sensor and an exhaust gas sensor, by means of which the accuracy of the exhaust gas sensor can be at least partly increased over its service life. For example, some embodiments include a method for operating an exhaust gas sensor (10), which comprises a main body (112), is arranged in an exhaust gas system of an internal combustion engine and comprises a pump cavity (30) that is arranged in the main body (12) and in which a pump electrode (34) is arranged, a measuring cavity (40) that is arranged in the main body (12), is connected to the pump cavity (30) and in which a measuring electrode (34) is arranged, and a reference cavity (50) that is arranged in the main body (12), is connected to the ambient air and in which a reference electrode (52) is arranged, wherein the method comprises: outputting oxygen from the measuring cavity (40) by applying a measurement current (IP2) to the measuring electrode (44) in such a way that a measurement voltage (V2) forming between the measuring electrode (44) and the reference electrode (52) is kept at a predetermined first setpoint value, outputting oxygen from the pump cavity (30) by applying a pump current (IP1) to the pump electrode (34) in such a way that an electrode voltage (V1) forming between the pump electrode (34) and the reference electrode (52) is kept at a predetermined second setpoint value, determining a nitrogen oxide value at least partly on the basis of the measurement current (IP2) applied to the measuring electrode (44), adapting the first setpoint value for the measurement voltage (V2) depending on the determined nitrogen oxide value, and/or adapting the second setpoint value for the electrode voltage (V1) depending on the determined nitrogen oxide value.

In some embodiments, adapting the first setpoint value comprises: increasing the first setpoint value for the measurement voltage (V2) if the nitrogen oxide value increases, and decreasing the first setpoint value for the measurement voltage (V2) if the nitrogen oxide value decreases.

In some embodiments, adapting the second setpoint value comprises: increasing the second setpoint value for the electrode voltage (V1) if the nitrogen oxide value decreases, and decreasing the second setpoint value for the electrode voltage (V1) if the nitrogen oxide value decreases.

In some embodiments, the first setpoint value is in the range of between approximately 400 mV and approximately 500 mV, in particular between approximately 420 mV and approximately 450 mV.

In some embodiments, the second setpoint value is in the range of between approximately 350 mV and approximately 450 mV, in particular between approximately 370 mV and approximately 400 mV.

In some embodiments, the method further comprises: determining a nitrogen oxide value of approximately 0 ppm, setting the first setpoint value for the measurement voltage (V2) to approximately 420 mV, and/or setting the second setpoint value for the electrode voltage (V1) to approximately 390 mV.

As another example, some embodiments include an exhaust gas sensor (10) to be arranged in an exhaust gas system of an internal combustion engine, wherein the exhaust gas sensor (10) comprises: a main body (12), a pump cavity (30) that is arranged in the main body (12) and in which a pump electrode (34) is arranged, a measuring cavity (40) that is arranged in the main body (12), is connected to the pump cavity (30) and in which a measuring electrode (34) is arranged, a reference cavity (50) that is arranged in the main body (12), is connected to the ambient air and in which a reference electrode (52) is arranged, and a control unit that is electrically connected to the pump electrode (34), the measuring electrode (44) and the reference electrode (52) and is designed to operate the exhaust gas sensor (10) according to a method as claimed in one of the preceding claims.

In some embodiments, the exhaust gas sensor (10) further comprises a further pump cavity (20) that is arranged in the main body (12), is connected to the exhaust gas and the pump cavity (30) and in which a further pump electrode (24) is arranged.

BRIEF DESCRIPTION OF THE DRAWINGS

Further features and objects of the present disclosure will become apparent to a person skilled in the art by putting the present teaching into practice and taking into consideration the accompanying drawings, in which.

DETAILED DESCRIPTION

Figure 1:
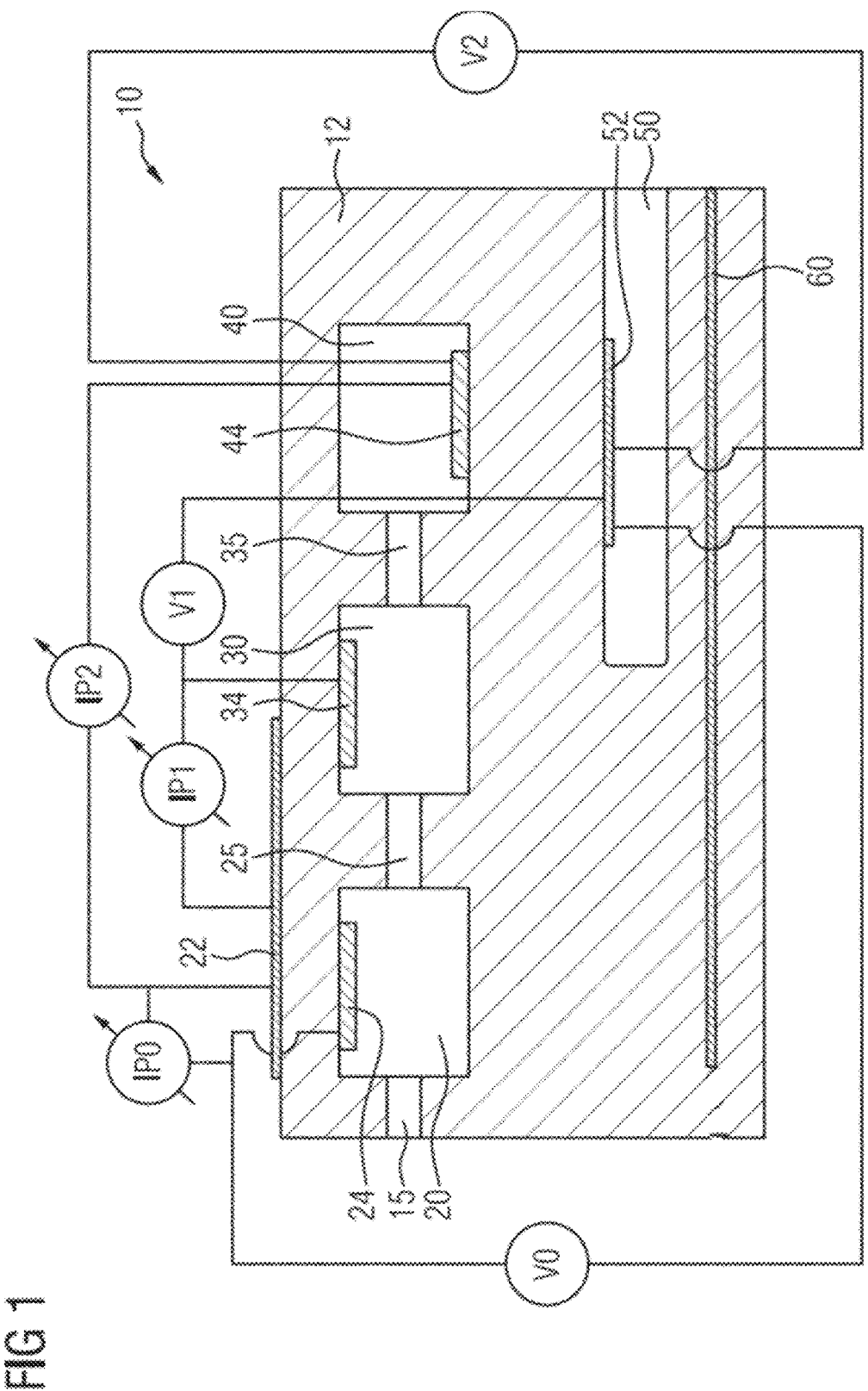
FIG. 1 shows a schematic sectional view through an exhaust gas sensor for an internal combustion engine of a vehicle, said exhaust gas sensor being illustrated by way of example in the form of a nitrogen oxide sensor incorporating teachings of the present disclosure.

Embodiments of the present disclosure may include dynamically adjusting the voltage setpoint values for the Nernst voltages during operation of an exhaust gas sensor, in particular nitrogen oxide sensor, depending on the present nitrogen oxide content in the exhaust gas and not, as was previously known from the prior art, predefining and maintaining the setpoint values for the Nernst voltages from the factory unchanged over the service life of the exhaust gas sensor. By way of example, in the case of low nitrogen oxide concentrations, such as less than 20 ppm, for example, the setpoint value for the measurement voltage that forms between the measuring electrode and the reference electrode by the application of a measurement current to the measuring electrode is able to be decreased and the setpoint value for the electrode voltage that forms between a pump electrode and the reference electrode by the application of a pump current to the pump electrode is able to be increased. On the one hand, the ion decomposition of the water present in the exhaust gas within the measuring cavity can be decreased by decreasing the setpoint value for the measurement voltage, and on the other hand, the oxygen offset within the associated pump cavity can be reduced by way of the increased setpoint value for the electrode voltage.

In some embodiments, in the case of higher nitrogen oxide concentrations, such as 1500 ppm, for example, the method includes increasing the setpoint value for the measurement voltage and to decrease the setpoint value for the electrode voltage. The increased setpoint value for the measurement voltage allows the nitrogen oxide decomposition at the measuring electrode within the measuring cavity to be stabilized, and decreasing the setpoint value for the electrode voltage allows unwanted decomposition of the nitrogen oxides at the pump electrode within the associated pump cavity to be decreased. This allows interfering properties of the exhaust gas sensor, such as static pressure cross-sensitivity and other cross-influences, for example, to be reduced and the measuring accuracy of the exhaust gas sensor to be increased.

Consequently, some embodiments include a method for operating an exhaust gas sensor, which comprises a main body, is arranged in an exhaust gas system of an internal combustion engine and comprises a pump cavity that is arranged in the main body and in which a pump electrode is arranged, a measuring cavity that is arranged in the main body, is connected to the pump cavity and in which a measuring electrode is arranged, and a reference cavity that is arranged in the main body, is connected to the ambient air and in which a reference electrode is arranged. The method according to the invention comprises outputting oxygen from the measuring cavity by applying a measurement current to the measuring electrode in such a way that a measurement voltage forming between the measuring electrode and the reference electrode is kept at a predetermined first setpoint value, outputting oxygen from the pump cavity by applying a pump current to the pump electrode in such a way that an electrode voltage forming between the pump electrode and the reference electrode is kept at a predetermined second setpoint value, determining a nitrogen oxide value at least partly on the basis of the measurement current applied to the measuring electrode, adapting the first setpoint value for the measurement voltage depending on the determined nitrogen oxide value, and/or adapting the second setpoint value for the electrode voltage depending on the determined nitrogen oxide value. In some embodiments, the exhaust gas sensor, for example a nitrogen oxide sensor, may be operated in such a way that the measurement voltage and/or electrode voltage are dynamically adapted and set for the following measuring cycles depending on the determined nitrogen oxide value.

In some embodiments, adjusting the first setpoint value comprises increasing the first setpoint value for the measurement voltage if the nitrogen oxide value increases, and decreasing the first setpoint value for the measurement voltage if the nitrogen oxide value decreases. Decreasing the setpoint value for the measurement voltage allows the ion decomposition of the water present in the exhaust gas within the measuring cavity to be decreased. In addition, an increased setpoint value for the measurement voltage allows the nitrogen oxide decomposition at the measuring electrode within the measuring cavity to be stabilized.

In some embodiments, adjusting the second setpoint value comprises increasing the second setpoint value for the electrode voltage if the nitrogen oxide value decreases, and decreasing the second setpoint value for the electrode voltage if the nitrogen oxide value decreases. The increased setpoint value for the electrode voltage allows the oxygen offset within the associated pump cavity to be reduced. Furthermore, decreasing the setpoint value for the electrode voltage allows unwanted decomposition of the nitrogen oxides at the pump electrode within the associated pump cavity to be decreased. Adapting the setpoint values for the measurement voltage and/or electrode voltage therefore allows interfering properties of the exhaust gas sensor, such as static pressure cross-sensitivity and other cross-influences, for example, to be reduced and the measuring accuracy of the exhaust gas sensor to be increased.

In some embodiments, the first setpoint value is in the range of between approximately 400 mV and approximately 500 mV, in particular between approximately 420 mV and approximately 450 mV.

In some embodiments, the second setpoint value is in the range of between approximately 350 mV and approximately 450 mV, in particular between approximately 370 mV and approximately 400 mV.

In some embodiments, the method according to the invention further comprises determining a nitrogen oxide value of approximately 0 ppm, setting the first setpoint value for the measurement voltage to approximately 420 mV and/or setting the second setpoint value for the electrode voltage to approximately 390 mV. In the presence of a substantially nitrogen oxide-free exhaust gas, the setpoint for the measurement voltage and/or the setpoint for the electrode voltage may be set back to the originally calibrated output value of approximately 420 mV or 390 mV.

In some embodiments, the exhaust gas sensor further comprises a further pump cavity that is arranged in the main body, is connected to the exhaust gas and the pump cavity and in which a further pump electrode is arranged. In such a configuration, the method further comprises outputting oxygen from the further pump cavity by applying a further pump current to the further pump electrode in such a way that a further electrode voltage forming between the further pump electrode and the reference electrode is kept at a predetermined third setpoint value, and adapting the third setpoint value for the further electrode voltage depending on the determined nitrogen oxide value.

In some embodiments, an exhaust gas sensor to be arranged in an exhaust gas system of an internal combustion engine is provided. The exhaust gas sensor comprises a main body, a pump cavity that is arranged in the main body and in which a pump electrode is arranged, a measuring cavity that is arranged in the main body, is connected to the pump cavity and in which a measuring electrode is arranged, a reference cavity that is arranged in the main body, is connected to the ambient air and in which a reference electrode is arranged, and a control unit that is electrically connected to the pump electrode, the measuring electrode and the reference electrode and is designed to operate the exhaust gas sensor according to one or more of the methods described herein.

In some embodiments, the exhaust gas sensor further comprises a further pump cavity that is arranged in the main body, is connected to the exhaust gas and the pump cavity and in which a further pump electrode is arranged.

In the context of the present disclosure, sensors that operate using amperometry, such as nitrogen oxide sensors, lambda probes and oxygen sensors, for example, are characterized in that their measurement principle is based on amperometry, i.e. on an electrochemical method for quantitatively determining chemical substances. In particular, an electric current is set at a working electrode in such a way that an electrochemical potential that is constant over time is established.

Furthermore, in the context of the present disclosure, the term "control" encompasses the control engineering terms "open-loop control" and "closed-loop control". A person skilled in the art will recognize in each case when open-loop control should be applied and when closed-loop control should be applied.

FIG. 1 shows an exemplary nitrogen oxide sensor 10, which represents an example of an exhaust gas sensor incorporating teachings of the present disclosure. Consequently, the teachings of the present disclosure may be used in the case of all sensors for internal combustion engines for vehicles that comprise a heating device, such as lambda probes and oxygen sensors, for example. In particular, the teachings are applicable to exhaust gas sensors that comprise a ceramic main support with at least one pair of electrodes attached thereto.

Referring to FIG. 1, a schematic sectional view of the exemplary nitrogen oxide sensor 10 is illustrated, which sensor is designed to be arranged in an exhaust gas tract of an internal combustion engine (not shown) and to quantitatively detect the nitrogen oxide content and/or the oxygen content in the exhaust gas of the internal combustion engine.

The nitrogen oxide sensor 10 comprises a main body 12 composed of a solid electrolyte, which may be formed from a mixed crystal composed of zirconium oxide and yttrium oxide and/or by a mixed crystal composed of zirconium oxide and calcium oxide. A mixed crystal composed of hafnium oxide, a mixed crystal composed of perovskite-based oxides or a mixed crystal composed of trivalent metal oxide may be used, such as aluminum oxide ($Al_2O_3$), for example. The main body 12 forms a sensor element of the exhaust gas sensor 10. The main body 12 may therefore also be referred to as a sensor element.

A first pump cavity 20, a second pump cavity 30 and a measuring cavity 40 are provided within the main body 12 of the nitrogen oxide sensor 10 illustrated by way of example. The first pump cavity 20 is connected to the exterior of the main body 12 via a connecting path 15. In particular, exhaust gas can flow or pass through the connecting path 15 into the first pump cavity 20. The second pump cavity 30 is connected to the first pump cavity 20 via a first diffusion path 25. The measuring cavity 40 is connected to the second pump cavity 30 via a second diffusion path 35.

The first diffusion path 25 and/or the second diffusion path 35 is provided, for example, in the form of a very thin slit through which the gas mixture can pass at a predetermined rate. Alternatively, the first diffusion path 25 and/or the second diffusion path 35 may be filled or padded with a porous filler to form a diffusion rate regulating layer.

The first diffusion path 25 and/or the second diffusion path 35 are designed in such a way that the gas mixture can only partially pass through them. Knowledge of the cross-sections of the first and/or second diffusion path 25, 35 and/or knowledge of the respective porous filler allows the diffusion rate through the first and/or second diffusion path 25, 35 to be determined and stipulated.

In an alternative configuration of the exhaust gas sensor, which, by way of example, is in the form of a nitrogen oxide sensor 10, only a pump cavity 20, 30 with a pump electrode 24, 34 and the measuring cavity 40 with the measuring electrode 44 are provided in the main body 12.

Moreover, a reference cavity 50 is formed in the main body 12, and is directly connected to the exterior of the main body 12. A reference electrode 52 is arranged within the reference cavity 50. In particular, the reference cavity 50 is connected to the ambient air, i.e. not to the exhaust gas, and is configured to form an oxygen reference for the various electrodes arranged in the nitrogen oxide sensor 10.

An exhaust gas electrode 22 (also called "P+" electrode) is arranged on an outer side of the main body 12. In particular, during measurement operation of the nitrogen oxide sensor 10, by applying a reference current to the exhaust gas electrode 22, the oxygen situated in the exhaust gas can be ionized and can flow through the main body 12 as oxygen ions to the reference electrode 52 and can be converted there into oxygen molecules in order to form an oxygen reference.

A first pump electrode 24 (also called "P−" electrode) is arranged within the first pump cavity 20. In particular, during measurement operation of the nitrogen oxide sensor 10, by applying a first pump current IP0 to the first pump electrode 24, the oxygen situated in the exhaust gas can be ionized within the first pump cavity 20 and can migrate or pass through the main body 12 as oxygen ions. On account of the oxygen ions output from the first pump cavity 20, a first electrode voltage or first Nernst voltage V0 forms indirectly between the first pump electrode 24 and the reference electrode 52. To put it more precisely, the first electrode voltage or the first Nernst voltage V0 forms directly from the residual oxygen still present in the first pump cavity 20.

A second pump electrode 34 (also called "M1" electrode) is arranged within the second pump cavity 30. Here, during measurement operation of the nitrogen oxide sensor 10, by applying a first pump current IP1 to the second pump electrode 34, the oxygen situated in the gas mixture can be ionized within the second pump cavity 30 and can migrate or pass through the main body 12 as oxygen ions. On account of the oxygen ions output from the second pump cavity 30, a second electrode voltage or second Nernst voltage V1 forms indirectly between the second pump electrode 34 and the reference electrode 52. To put it more precisely, the second electrode voltage or the second Nernst voltage V1 forms directly from the residual oxygen still present in the second pump cavity 30.

A measuring electrode 44 (also called "M2" electrode) is arranged within the measuring cavity 40, and is designed, during measurement operation of the nitrogen oxide sensor 10, upon the application of a measurement current IP2, to ionize the oxygen and/or nitrogen oxides present within the measuring cavity 40, such that the oxygen ions can migrate or pass through the main body 12. On account of the oxygen ions output or pumped out from the measuring cavity 40, a third electrode voltage or third Nernst voltage or measurement voltage V2 forms between the measuring electrode 44 and the reference electrode 52 and should be kept at a constant value by the application of the measurement current IP2 to the measuring electrode 44. To put it more precisely, the third electrode voltage or the third Nernst voltage or measurement voltage V2 forms directly from the residual oxygen still present in the measuring cavity 40. The applied measurement current IP2 is then and indication of the oxygen content situated within the exhaust gas.

The nitrogen oxide sensor 10 shown in FIG. 1, which represents an example of a sensor based on the amperometric measurement principle, thus comprises three relevant electrode pairs, namely the first electrode pair consisting of the first pump electrode 24 and the exhaust gas electrodes 22, a second electrode pair consisting of the second pump electrode 34 and the exhaust gas electric 22, and a third electrode pair consisting of the measuring electrode 44 and the exhaust gas electrode 22.

The pump currents IP0 and IP1 applied to the first and second pump electrodes 24, 34 are set in such a way that preferably only the oxygen present in the gas mixture is ionized, but not the nitrogen oxides in the gas mixture. In particular, the first pump electrode 24 is designed, during normal operation of the nitrogen oxide sensor 10, to pump almost all of the oxygen from the exhaust gas or to permit a predetermined oxygen slippage from the first pump cavity 20 into the second pump cavity 30. The second pump electrode 34 is designed to ionize the oxygen that has not yet been pumped out from the first pump cavity 20 and to guide it away, such that the oxygen ions bound in the gas mixture that is present in the measuring cavity 40 are only bound to nitrogen and are in the form of nitrogen oxides. The measuring electrode 44 is configured to ionize the nitrogen oxides, wherein the measurement current IP2 applied to the measuring electrode 44 is a measure of the nitrogen oxide content in the exhaust gas.

Furthermore, a heating device 60 is arranged within the main body 12, and is configured to heat the main body 12 to a predetermined operating temperature and to keep it at this temperature, for example at approximately 850° C.

The mode of operation for determining the nitrogen oxide content in the exhaust gas of the internal combustion engine by means of the nitrogen oxide sensor 10 disclosed, to which reference is made at this juncture. The closed-loop control principle, which is known from the prior art, for the nitrogen oxide sensor 10 of FIG. 1 is in particular characterized in that the respective electrode voltages or Nernst voltages V0, V1, V2 are kept at respectively predetermined setpoint values, which are unchangeable over the service life of the nitrogen oxide sensor 10 and are predetermined at the factory on a one-off basis, by applying and adapting the pump currents IP0, IP1 and the measurement current IP2. To this end, the nitrogen oxide sensor 10 comprises a control unit (not shown), which is electrically connected to the electrodes 22, 24, 34, 44, 52 and is designed to actuate the respective electrodes with electric current so that the respective electrode voltages or measurement voltage or Nernst voltages V0, V1, V2 can be kept at the predetermined setpoint values.

In some embodiments, the respective electrode voltages or measurement voltage or Nernst voltages V0, V1, V2 to be dynamically adapted by applying and adapting the pump currents IP0, IP1 and the measurement current IP2 depending on the previously determined nitrogen oxide value. This means that the setpoint values, predefined at the factory, for the electrode voltages or measurement voltage or Nernst voltages V0, V1, V2 are dynamically adapted during operation of the exhaust gas sensor, in particular nitrogen oxide sensor 10, depending on the nitrogen oxide value. In particular, provision is made according to the invention for the setpoint value for the measurement voltage V2 and the setpoint value for the electrode voltage V1 to be dynamically adapted depending on the determined nitrogen oxide value.

Figure 2:
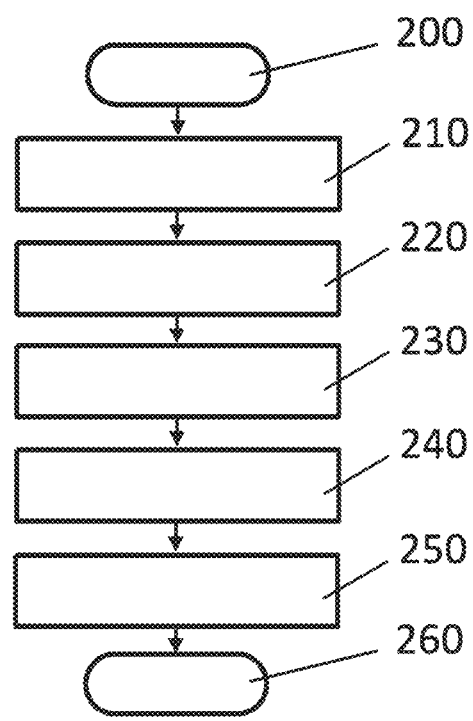
FIG. 2 shows an exemplary flowchart of a method incorporating teachings of the present disclosure for operating an exhaust gas sensor.

Referring to FIG. 2, a flowchart of an example method incorporating teachings of the present disclosure for operating the nitrogen oxide sensor 10 of FIG. 1 is shown.

The method of FIG. 2 starts at step 200 and then proceeds to step 210 in which first the oxygen is output from the gas mixture present in the second pump cavity 30 by applying the second pump current IP1 to the pump electrode 34. To this end, the pump current IP1 applied to the pump electrode 34 is controlled in such a way that the second electrode voltage V1 is kept at a predetermined setpoint value. In particular, the oxygen present in the gas mixture may be ionized as a result, such that the gas mixture present in the measuring cavity 40 is essentially free of oxygen after flowing through the second pump cavity 30.

In a subsequent step 220, the measurement current IP2 applied to the measuring electrode 44 is controlled in such a way that the measurement voltage V2 is kept at a predetermined setpoint value, as a result of which the nitrogen oxides in the gas mixture within the measuring cavity 40 are decomposed or ionized. The measurement current IP2 can then indicate the nitrogen oxide content in the exhaust gas. Steps 210 and 220 therefore indicate the standard operation of the nitrogen oxide sensor 10, wherein the initially predefined and predetermined setpoint values for the electrode voltage V1 and the measurement voltage V2 may be used at the start.

In a subsequent step 230, the nitrogen oxide content present in the exhaust gas may then be determined from the measurement voltage IP2.

In a subsequent step 240, the first setpoint value for the measurement voltage V2 may be adapted depending on the nitrogen oxide value determined in step 230. In a subsequent step 250, the setpoint value for the electrode voltage V1 is adapted depending on the nitrogen oxide value determined in step 230.

In the case of low nitrogen oxide values, such as 20 ppm, for example, provision is made to decrease the first setpoint value for the measurement voltage V2 and to increase the second setpoint value for the electrode voltage V1. This prevents the water present within the measuring cavity 40 from also being decomposed. At the same time, increasing the setpoint value for the electrode voltage V1 allows an oxygen offset to be reduced, wherein the oxygen offset describes the oxygen slippage through the pump cavities 20, 30 into the measuring cavity 40.

If, however, the nitrogen oxide value determined in step 230 is large, such as 1500 ppm, for example, the method may include increasing the first setpoint value for the measurement voltage V2 and decreasing the second setpoint value for the electrode voltage V1. Increasing the first setpoint value for the measurement voltage V2 allows the nitrogen oxide decomposition at the measuring electrode 44 to be stabilized. This means that the IP2/V2 characteristic reaches a plateau or saturation depending on the concentration from a certain V2. This effect increases as the nitrogen oxide content increases. At the same time, decreasing the second setpoint value for the electrode voltage V1 allows unwanted nitrogen oxide decomposition in the pump cavity 30 at the pump electrode 34 to be decreased. The accuracy of the nitrogen oxide sensor 10 can therefore be improved by decreasing the static pressure cross-sensitivity of the nitrogen oxide sensor 10 and other cross-influences.

Provision is furthermore made to set the setpoint values for the measurement voltage V2 and electrode voltage V1 to their factory-set setpoint values during operating times of the internal combustion engine in which the exhaust gas is essentially free of nitrogen oxide, that is to say approximately 0 ppm of nitrogen oxides. By way of example, these can be 420 mV in each case. If the exhaust gas then comprises nitrogen oxide again and consequently increases from 0 ppm to an exemplary value of 100 ppm, the measurement voltage V2 may then be set to an increased value, such as 425 mV, for example. Consequently, in this case, the setpoint values for the measurement voltage V2 and the setpoint value for the electrode voltage V1 are adjusted according to the nitrogen oxides.

What is claimed is:

1. A method for operating an exhaust gas sensor with a main body arranged in an exhaust gas system of an internal combustion engine, a pump cavity in the main body and housing a pump electrode, a measuring cavity in the main body connected to the pump cavity and housing a measuring electrode, and a reference cavity in the main body connected to ambient air and housing a reference electrode, the method comprising:
discharging oxygen from the measuring cavity by applying a measurement current to the measuring electrode so a measurement voltage between the measuring electrode and the reference electrode is kept at a predetermined first setpoint value;
discharging oxygen from the pump cavity by applying a pump current to the pump electrode so an electrode voltage between the pump electrode and the reference electrode is kept at a predetermined second setpoint value;
determining a nitrogen oxide value based at least in part on a value of the measurement current; and
adapting at least one of the first setpoint value for the measurement voltage based on the determined nitrogen oxide value or the second setpoint value for the electrode voltage based on the determined nitrogen oxide value.

2. The method as claimed in claim 1, wherein:
the first setpoint value is adapted; and
adapting the first setpoint value comprises:
increasing the first setpoint value for the measurement voltage if the nitrogen oxide value increases; and
decreasing the first setpoint value for the measurement voltage if the nitrogen oxide value decreases.

3. The method as claimed in claim 1, wherein:
the second setpoint value is adapted; and
adapting the second setpoint value comprises:
increasing the second setpoint value for the electrode voltage if the nitrogen oxide value decreases; and
decreasing the second setpoint value for the electrode voltage if the nitrogen oxide value decreases.

4. The method as claimed in claim 1, wherein the first setpoint value is in the range between 400 mV and 500 mV.

5. The method as claimed in claim 1, wherein the second setpoint value is in the range between 350 mV and 450 mV.

6. The method as claimed in claim 1, further comprising:
determining a nitrogen oxide value of approximately 0 ppm;
setting the first setpoint value for the measurement voltage to approximately 420 mV; and/or
setting the second setpoint value for the electrode voltage to approximately 390 mV.

7. An exhaust gas sensor for an exhaust gas system of an internal combustion engine, the exhaust gas sensor comprising:
a main body;
a pump electrode arranged in a pump cavity of the main body;
a measuring electrode arranged in a measuring cavity of the main body and connected to the pump cavity;
a reference electrode in a reference cavity of the main body and connected to ambient air; and
a control unit electrically connected to the pump electrode, the measuring electrode, and the reference electrode and designed to:
discharge oxygen from the measuring cavity by applying a measurement current to the measuring electrode so a measurement voltage between the measuring electrode and the reference electrode is kept at a predetermined first setpoint value;
discharge oxygen from the pump cavity by applying a pump current to the pump electrode so an electrode voltage between the pump electrode and the reference electrode is kept at a predetermined second setpoint value;
determine a nitrogen oxide value based at least in part on a value of the measurement current; and
adapt at least one of: the first setpoint value for the measurement voltage based on the determined nitrogen oxide value and the second setpoint value for the electrode voltage based on the determined nitrogen oxide value.

8. The exhaust gas sensor as claimed in claim 7, further comprising a further pump electrode in a further pump cavity in the main body connected to the exhaust gas and the pump cavity.

* * * * *